(12) United States Patent
Weaver et al.

(10) Patent No.: US 11,628,243 B2
(45) Date of Patent: *Apr. 18, 2023

(54) PRESSURE ACTUATED VALVE WITH IMPROVED BIASING MEMBER

(71) Applicant: AngioDynamics, Inc., Latham, NY (US)

(72) Inventors: Karla Weaver, Framingham, MA (US); Jim Culhane, Westboro, MA (US)

(73) Assignee: AngioDynamics, Inc., Latham, NY (US)

( * ) Notice: Subject to any disclaimer, the term of this patent is extended or adjusted under 35 U.S.C. 154(b) by 841 days.

This patent is subject to a terminal disclaimer.

(21) Appl. No.: 16/666,870

(22) Filed: Oct. 29, 2019

(65) Prior Publication Data

US 2020/0061279 A1    Feb. 27, 2020

Related U.S. Application Data

(63) Continuation of application No. 14/857,962, filed on Sep. 18, 2015, now Pat. No. 10,500,329, which is a
(Continued)

(51) Int. Cl.
*A61M 1/36* (2006.01)
*A61M 25/00* (2006.01)
(Continued)

(52) U.S. Cl.
CPC ........ *A61M 1/3653* (2013.01); *A61M 1/3659* (2014.02); *A61M 1/3661* (2014.02);
(Continued)

(58) Field of Classification Search
CPC .............. A61M 1/3653; A61M 1/3659; A61M 1/3661; A61M 25/0028; A61M 25/0029;
(Continued)

(56) References Cited

U.S. PATENT DOCUMENTS

| 26,235 A | 11/1859 | Scott |
| 500,745 A | 7/1893 | Rogers |

(Continued)

FOREIGN PATENT DOCUMENTS

| CN | 102155808 | 8/2011 |
| DE | 3048203 | 7/1982 |

(Continued)

OTHER PUBLICATIONS

Asch, "Venous access: options, approaches and issues," Can. Assoc. Radiol. J., vol. 52, No. 3, pp. 153-164 (2001) 12 pages.
(Continued)

*Primary Examiner* — Leslie R Deak
(74) *Attorney, Agent, or Firm* — DLA Piper LLP (US)

(57) ABSTRACT

A valve for controlling material flow through a catheter, comprises a first flexible member including a first moveable element, wherein, when the first moveable element is in the open position, material may flow past the first flexible member through a first lumen of the catheter and, when the first moveable element is in the closed position, flow through the first lumen is prevented and a first biasing member coupled to the first flexible member for biasing the first moveable member toward the closed position.

20 Claims, 4 Drawing Sheets

Related U.S. Application Data continuation of application No. 13/961,237, filed on Aug. 7, 2013, now abandoned, which is a continuation of application No. 12/250,920, filed on Oct. 14, 2008, now Pat. No. 8,529,523, which is a continuation of application No. 10/608,660, filed on Jun. 27, 2003, now Pat. No. 7,435,236.

(51) Int. Cl.
    *A61M 39/24*    (2006.01)
    *F16K 15/14*    (2006.01)
    *A61M 39/22*    (2006.01)

(52) U.S. Cl.
    CPC .... *A61M 25/0028* (2013.01); *A61M 25/0029* (2013.01); *A61M 39/22* (2013.01); *A61M 39/24* (2013.01); *F16K 15/147* (2013.01); *A61M 2025/0031* (2013.01); *A61M 2039/2433* (2013.01); *Y10T 137/7882* (2015.04)

(58) Field of Classification Search
    CPC .................. A61M 39/22; A61M 39/24; A61M 2025/0031; A61M 2039/2433; F16K 15/147; Y10T 137/7882
    See application file for complete search history.

(56) References Cited

U.S. PATENT DOCUMENTS

| | | |
|---|---|---|
| 1,142,525 A | 6/1915 | Maag |
| 1,244,379 A | 10/1917 | Short |
| 1,989,145 A | 1/1935 | Newby |
| 2,122,299 A | 6/1938 | Sloan |
| 2,446,571 A | 8/1948 | Browne |
| 2,720,881 A | 10/1955 | Jones |
| 2,755,060 A | 7/1956 | Raymond |
| 2,841,166 A | 7/1958 | Auzin |
| 3,020,913 A | 2/1962 | Heyer |
| 3,111,125 A | 11/1963 | Schulte |
| 3,113,586 A | 12/1963 | Edmark, Jr. |
| 3,118,468 A | 1/1964 | Bochan |
| 3,159,175 A | 12/1964 | Macmillan |
| 3,159,176 A | 12/1964 | Russell |
| RE26,235 E | 7/1967 | Woodford |
| 3,422,844 A | 1/1969 | Grise |
| 3,477,438 A | 11/1969 | Allen |
| 3,514,438 A | 5/1970 | Bixler |
| 3,525,357 A | 8/1970 | Koreski |
| 3,621,557 A | 11/1971 | Cushman |
| 3,662,955 A | 5/1972 | Takanashi |
| 3,669,323 A | 6/1972 | Harker |
| 3,673,612 A | 7/1972 | Merrill |
| 3,674,183 A | 7/1972 | Venable |
| 3,710,942 A | 1/1973 | Rosenberg |
| 3,788,327 A | 1/1974 | Donowitz |
| 3,811,466 A | 5/1974 | Ohringer |
| 3,827,456 A | 8/1974 | Sheppard |
| 3,848,579 A | 11/1974 | Villa |
| 3,885,561 A | 5/1975 | Cami |
| 3,888,249 A | 6/1975 | Spencer |
| 3,941,149 A | 3/1976 | Mittleman |
| 3,955,594 A | 5/1976 | Snow |
| 3,964,509 A | 6/1976 | Daubenberger |
| 4,000,740 A | 1/1977 | Mittleman |
| 4,072,146 A | 2/1978 | Howes |
| 4,134,402 A | 1/1979 | Mahurkar |
| 4,137,152 A | 1/1979 | Chester |
| 4,142,525 A | 3/1979 | Binard |
| 4,143,853 A | 3/1979 | Abramson |
| 4,176,678 A | 12/1979 | Marchaix et al. NAME |
| 4,232,677 A | 11/1980 | Leibinsohn |
| 4,244,379 A | 1/1981 | Smith |
| 4,327,722 A | 5/1982 | Groshong |
| 4,342,315 A | 8/1982 | Jackson |
| 4,387,879 A | 6/1983 | Tauschinski |
| 4,405,316 A | 9/1983 | Mittleman |
| 4,417,888 A | 11/1983 | Cosentino |
| 4,424,058 A | 1/1984 | Parsons |
| 4,424,833 A | 1/1984 | Spector |
| 4,431,426 A | 2/1984 | Groshong |
| 4,434,810 A | 3/1984 | Atkinson |
| 4,447,237 A | 5/1984 | Frisch |
| 4,465,102 A | 8/1984 | Rupp |
| 4,468,224 A | 8/1984 | Enzmann |
| 4,475,898 A | 10/1984 | Brodner |
| 4,502,502 A | 3/1985 | Krug |
| 4,524,805 A | 6/1985 | Hoffman |
| 4,529,399 A | 7/1985 | Groshong |
| 4,543,087 A | 9/1985 | Sommercorn |
| 4,549,879 A | 10/1985 | Groshong |
| 4,552,553 A | 11/1985 | Schulte |
| 4,559,046 A | 12/1985 | Groshong |
| 4,610,276 A | 9/1986 | Paradis |
| 4,610,665 A | 9/1986 | Matsumoto |
| 4,616,768 A | 10/1986 | Flier |
| 4,625,245 A | 11/1986 | White |
| 4,626,245 A | 12/1986 | Weinstein |
| 4,646,945 A | 3/1987 | Steiner |
| 4,668,221 A | 5/1987 | Luther |
| 4,671,796 A | 6/1987 | Groshong |
| 4,673,393 A | 6/1987 | Suzuki |
| 4,681,572 A | 7/1987 | Tokarz |
| 4,692,141 A | 9/1987 | Mahurkar |
| 4,692,146 A | 9/1987 | Hilger |
| 4,701,166 A | 10/1987 | Groshong |
| 4,722,725 A | 2/1988 | Sawyer |
| 4,728,006 A | 3/1988 | Drobish |
| 4,737,152 A | 4/1988 | Alchas |
| 4,753,640 A | 6/1988 | Nichols |
| 4,790,817 A | 12/1988 | Luther |
| 4,790,832 A | 12/1988 | Lopez |
| 4,798,594 A | 1/1989 | Hillstead |
| 4,801,297 A | 1/1989 | Mueller |
| 4,809,679 A | 3/1989 | Shimonaka |
| 4,813,934 A | 3/1989 | Engelson |
| 4,842,591 A | 6/1989 | Luther |
| 4,908,028 A | 3/1990 | Colon |
| 4,944,726 A | 7/1990 | Hilal |
| 4,946,448 A | 8/1990 | Richmond |
| 4,950,252 A | 8/1990 | Luther |
| 4,960,412 A | 10/1990 | Fink |
| 4,973,319 A | 11/1990 | Melsky |
| 4,986,814 A | 1/1991 | Burney |
| 4,991,745 A | 2/1991 | Brown |
| 4,994,046 A | 2/1991 | Wesson |
| 4,995,863 A | 2/1991 | Nichols |
| 4,998,919 A | 3/1991 | Schnepp-Pesch |
| 5,000,745 A | 3/1991 | Guest |
| 5,009,391 A | 4/1991 | Steigerwald |
| 5,030,210 A | 7/1991 | Alchas |
| 5,062,836 A | 11/1991 | Wendell |
| 5,084,015 A | 1/1992 | Moriuchi |
| 5,085,635 A | 2/1992 | Cragg |
| 5,098,405 A | 3/1992 | Peterson |
| 5,125,893 A | 6/1992 | Dryden |
| 5,143,853 A | 9/1992 | Walt |
| 5,147,332 A | 9/1992 | Moorehead |
| 5,149,327 A | 9/1992 | Oshiyama |
| 5,167,638 A | 12/1992 | Felix |
| 5,169,393 A | 12/1992 | Moorehead |
| 5,176,652 A | 1/1993 | Littrell |
| 5,176,662 A | 1/1993 | Bartholomew |
| 5,201,722 A | 4/1993 | Moorehead |
| 5,201,772 A | 4/1993 | Maxwell |
| 5,205,834 A | 4/1993 | Moorehead |
| 5,215,538 A | 6/1993 | Larkin |
| 5,249,598 A | 10/1993 | Schmidt |
| 5,253,765 A | 10/1993 | Moorehead |
| 5,254,086 A | 10/1993 | Palmer |
| 5,255,676 A | 10/1993 | Russo |
| 5,324,274 A | 6/1994 | Martin |
| 5,330,424 A | 7/1994 | Palmer |
| 5,336,203 A | 8/1994 | Goldhardt |

(56) References Cited

U.S. PATENT DOCUMENTS

| | | |
|---|---|---|
| 5,360,407 A | 11/1994 | Leonard |
| 5,370,624 A | 12/1994 | Edwards |
| 5,395,352 A | 3/1995 | Penny |
| 5,396,925 A | 3/1995 | Poli |
| 5,399,168 A | 3/1995 | Wadsworth, Jr. |
| 5,401,255 A | 3/1995 | Sutherland |
| D357,735 S | 4/1995 | McPhee |
| 5,405,340 A | 4/1995 | Fageol |
| 5,411,491 A | 5/1995 | Goldhardt |
| 5,453,097 A | 9/1995 | Paradis |
| 5,454,784 A | 10/1995 | Atkinson |
| 5,469,805 A | 11/1995 | Gibbs |
| 5,470,305 A | 11/1995 | Arnett |
| 5,484,420 A | 1/1996 | Russo |
| 5,542,923 A | 8/1996 | Ensminger |
| 5,545,150 A | 8/1996 | Danks |
| 5,554,136 A | 9/1996 | Luther |
| 5,562,618 A | 10/1996 | Cai |
| 5,571,093 A | 11/1996 | Cruz |
| 5,575,769 A | 11/1996 | Vaillancourt |
| 5,619,393 A | 4/1997 | Summerfelt |
| 5,624,395 A | 4/1997 | Mikhail |
| 5,637,099 A | 6/1997 | Durdin |
| 5,667,500 A | 9/1997 | Palmer |
| 5,707,357 A | 1/1998 | Mikhail |
| 5,743,873 A | 4/1998 | Cai |
| 5,743,884 A | 4/1998 | Hasson |
| 5,743,894 A | 4/1998 | Swisher |
| 5,752,928 A | 5/1998 | De Roulhac |
| 5,752,938 A | 5/1998 | Flatland |
| 5,769,107 A | 6/1998 | Woodruff |
| 5,803,078 A | 9/1998 | Brauner |
| 5,807,349 A | 9/1998 | Person |
| 5,810,789 A | 9/1998 | Powers |
| 5,843,044 A | 12/1998 | Moorehead |
| 5,853,397 A | 12/1998 | Shemesh |
| 5,858,003 A | 1/1999 | Atala |
| 5,865,308 A | 2/1999 | Qin |
| 5,868,703 A | 2/1999 | Bertolero |
| 5,944,698 A | 8/1999 | Fischer |
| 5,984,902 A | 11/1999 | Moorehead |
| 5,989,233 A | 11/1999 | Yoon |
| 6,033,393 A | 3/2000 | Balbierz |
| 6,045,734 A | 4/2000 | Luther |
| 6,050,934 A | 4/2000 | Mikhail |
| 6,056,717 A | 5/2000 | Finch |
| 6,062,244 A | 5/2000 | Arkans |
| 6,081,106 A | 6/2000 | Camerlo |
| 6,092,551 A | 7/2000 | Bennett |
| 6,099,505 A | 8/2000 | Ryan |
| 6,110,154 A | 8/2000 | Shimomura |
| 6,120,483 A | 9/2000 | Davey |
| 6,152,129 A | 11/2000 | Berthon-Jones |
| 6,152,909 A | 11/2000 | Bagaoisan |
| 6,167,886 B1 | 1/2001 | Engel |
| 6,171,287 B1 | 1/2001 | Lynn |
| 6,210,366 B1 | 4/2001 | Sanfilippo, II |
| 6,227,200 B1 | 5/2001 | Crump |
| 6,270,489 B1 | 8/2001 | Wise |
| 6,296,316 B1 | 10/2001 | Hann |
| 6,306,124 B1 | 10/2001 | Jones |
| 6,322,541 B2 | 11/2001 | West |
| 6,364,861 B1 | 4/2002 | Feith |
| 6,364,867 B2 | 4/2002 | Wise |
| 6,375,637 B1 | 4/2002 | Campbell |
| 6,415,793 B1 | 7/2002 | Kretz |
| 6,436,077 B1 | 8/2002 | Davey |
| 6,442,415 B1 | 8/2002 | Bis |
| 6,446,671 B2 | 9/2002 | Armenia |
| 6,508,791 B1 | 1/2003 | Guerrero |
| 6,551,270 B1 | 4/2003 | Bimbo |
| 6,610,031 B1 | 8/2003 | Chin |
| 6,726,063 B2 | 4/2004 | Stull |
| 6,786,884 B1 | 9/2004 | DeCant, Jr. |
| 6,874,999 B2 | 4/2005 | Dai |
| 6,929,631 B1 | 8/2005 | Brugger |
| 6,953,450 B2 | 10/2005 | Baldwin |
| 6,994,314 B2 | 2/2006 | Garnier |
| 7,025,744 B2 | 4/2006 | Utterberg |
| 7,081,106 B1 | 7/2006 | Guo |
| 7,252,652 B2 | 8/2007 | Moorehead |
| 7,291,133 B2 | 11/2007 | Kindler |
| 7,316,655 B2 | 1/2008 | Garibotto |
| 7,435,236 B2 | 10/2008 | Weaver |
| D595,846 S | 7/2009 | Racz |
| D596,288 S | 7/2009 | Racz |
| 7,601,141 B2 | 10/2009 | Dikeman |
| 7,637,893 B2 | 12/2009 | Christensen |
| 7,713,250 B2 | 5/2010 | Harding |
| 7,731,700 B1 | 6/2010 | Schytte |
| 7,758,541 B2 | 7/2010 | Wallace |
| 7,931,619 B2 | 4/2011 | Diamond |
| 7,947,032 B2 | 5/2011 | Harding |
| 7,951,121 B2 | 5/2011 | Weaver |
| 7,988,679 B2 | 8/2011 | Daly |
| 7,993,327 B2 | 8/2011 | Casey, II |
| D644,731 S | 9/2011 | Fangrow, Jr. |
| 8,034,035 B2 | 10/2011 | Weaver |
| 8,079,987 B2 | 12/2011 | Moorehead |
| 8,083,721 B2 | 12/2011 | Miller |
| 8,105,314 B2 | 1/2012 | Fangrow, Jr. |
| 8,187,234 B2 | 5/2012 | Weaver |
| 8,257,321 B2 | 9/2012 | Lareau |
| 8,291,936 B2 | 10/2012 | Carmody |
| 8,328,768 B2 | 12/2012 | Quigley |
| 8,337,470 B2 | 12/2012 | Prasad |
| 8,343,113 B2 | 1/2013 | Hokanson |
| 8,377,011 B2 | 2/2013 | Weaver |
| 8,398,607 B2 | 3/2013 | Fangrow, Jr. |
| 8,444,628 B2 | 5/2013 | Fangrow, Jr. |
| 8,454,574 B2 | 6/2013 | Weaver |
| 8,454,579 B2 | 6/2013 | Fangrow, Jr. |
| 8,523,821 B2 | 9/2013 | Miller |
| 8,529,523 B2 | 9/2013 | Weaver |
| 8,540,685 B2 | 9/2013 | Moorehead |
| 8,585,660 B2 | 11/2013 | Murphy |
| 8,603,070 B1 | 12/2013 | Lareau |
| 8,628,515 B2 | 1/2014 | Fangrow, Jr. |
| 8,679,074 B2 | 3/2014 | Daly |
| 8,726,931 B2 | 5/2014 | Buiser |
| 8,753,320 B2 | 6/2014 | Miller |
| 8,758,306 B2 | 6/2014 | Lopez |
| 8,784,402 B1 | 7/2014 | Lareau |
| 8,789,558 B2 | 7/2014 | Volker |
| 8,870,850 B2 | 10/2014 | Fangrow, Jr. |
| 8,876,797 B2 | 11/2014 | Lareau |
| 8,926,571 B1 | 1/2015 | Keith |
| D722,155 S | 2/2015 | Wiegel |
| D722,156 S | 2/2015 | Wiegel |
| D722,157 S | 2/2015 | Wiegel |
| 9,044,541 B2 | 6/2015 | Blanchard |
| 9,186,494 B2 | 11/2015 | Fangrow |
| 9,192,753 B2 | 11/2015 | Lopez |
| 9,192,755 B2 | 11/2015 | Ravenscroft |
| 9,205,243 B2 | 12/2015 | Lopez |
| 9,206,283 B1 | 12/2015 | Santerre |
| 9,238,129 B2 | 1/2016 | Fangrow, Jr. |
| D752,215 S | 3/2016 | Blennnow |
| 9,278,206 B2 | 3/2016 | Fangrow |
| D757,259 S | 5/2016 | Duck |
| 9,447,892 B2 | 9/2016 | Lareau |
| 10,500,329 B2 * | 12/2019 | Weaver .................. A61M 39/22 |
| 2001/0023333 A1 | 9/2001 | Wise |
| 2001/0037079 A1 | 11/2001 | Burbank |
| 2002/0010425 A1 | 1/2002 | Guo |
| 2002/0016584 A1 | 2/2002 | Wise |
| 2002/0026145 A1 | 2/2002 | Bagaoisan |
| 2002/0111662 A1 | 8/2002 | Iaizzo |
| 2002/0121530 A1 | 9/2002 | Socier |
| 2002/0156430 A1 | 10/2002 | Haarala |
| 2002/0157664 A1 | 10/2002 | Fugelsang |
| 2002/0165492 A1 | 11/2002 | Davey |
| 2002/0193752 A1 | 12/2002 | Lynn |
| 2003/0014015 A1 | 1/2003 | Tansey |

(56) References Cited

U.S. PATENT DOCUMENTS

| | | |
|---|---|---|
| 2003/0122095 A1 | 7/2003 | Wilson |
| 2003/0189067 A1 | 10/2003 | Stull |
| 2003/0195478 A1 | 10/2003 | Russo |
| 2004/0034324 A1 | 2/2004 | Seese |
| 2004/0064128 A1 | 4/2004 | Raijman |
| 2004/0102738 A1 | 5/2004 | Dikeman |
| 2004/0108479 A1 | 6/2004 | Garnier |
| 2004/0186444 A1 | 9/2004 | Daly |
| 2004/0193119 A1 | 9/2004 | Canaud |
| 2004/0210194 A1 | 10/2004 | Bonnette |
| 2004/0267185 A1 | 12/2004 | Weaver |
| 2005/0010176 A1 | 1/2005 | Dikeman |
| 2005/0027261 A1 | 2/2005 | Weaver |
| 2005/0043703 A1 | 2/2005 | Nordgren |
| 2005/0049555 A1 | 3/2005 | Moorehead |
| 2005/0149116 A1 | 7/2005 | Edwards |
| 2005/0165364 A1 | 7/2005 | DiMatteo |
| 2005/0171488 A1 | 8/2005 | Weaver |
| 2005/0171490 A1 | 8/2005 | Weaver |
| 2005/0171510 A1 | 8/2005 | DiCarlo |
| 2005/0283122 A1 | 12/2005 | Nordgren |
| 2006/0129092 A1 | 6/2006 | Hanlon |
| 2006/0135949 A1 | 6/2006 | Rome |
| 2006/0149189 A1 | 7/2006 | Diamond |
| 2006/0149211 A1 | 7/2006 | Simpson |
| 2006/0149214 A1 | 7/2006 | Breiter |
| 2007/0161940 A1 | 7/2007 | Blanchard |
| 2007/0161970 A1 | 7/2007 | Spohn |
| 2007/0163664 A1 | 7/2007 | Mijers |
| 2007/0276313 A1 | 11/2007 | Moorehead |
| 2008/0097341 A1 | 4/2008 | Casey |
| 2008/0108956 A1 | 5/2008 | Lynn |
| 2008/0200837 A1 | 8/2008 | Frazier |
| 2009/0177187 A1 | 7/2009 | Weaver Quigley |
| 2009/0292252 A1 | 11/2009 | Lareau |
| 2011/0062703 A1 | 3/2011 | Lopez |
| 2011/0087093 A1 | 4/2011 | Buiser |
| 2011/0118612 A1 | 5/2011 | Miller |
| 2011/0264054 A1 | 10/2011 | Miller |
| 2011/0313367 A1 | 12/2011 | Daly |
| 2011/0313368 A1 | 12/2011 | Weaver |
| 2012/0271247 A1 | 10/2012 | Weaver |
| 2012/0325351 A1 | 12/2012 | Volker |
| 2013/0060200 A1 | 3/2013 | Dalton |
| 2013/0220462 A1 | 8/2013 | Lareau |
| 2013/0338608 A1 | 12/2013 | Moorehead |
| 2014/0081285 A1 | 3/2014 | Kucklick |
| 2014/0163516 A1 | 6/2014 | Lareau |
| 2015/0135554 A1 | 5/2015 | Smith |
| 2016/0008530 A1 | 1/2016 | Weaver |
| 2016/0121041 A1 | 5/2016 | Weaver |

FOREIGN PATENT DOCUMENTS

| | | |
|---|---|---|
| DE | 20208420 | 10/2002 |
| EP | 0128525 | 12/1984 |
| EP | 0128625 | 12/1984 |
| EP | 0198962 | 10/1986 |
| EP | 0337617 | 10/1989 |
| EP | 0366814 | 5/1990 |
| EP | 0474069 | 3/1992 |
| EP | 0864336 | 9/1998 |
| EP | 0882466 | 12/1998 |
| EP | 0930082 | 7/1999 |
| EP | 1016431 | 7/2000 |
| EP | 2720881 | 4/2014 |
| EP | 2755060 | 7/2014 |
| FR | 2508008 | 12/1982 |
| FR | 2718969 | 10/1995 |
| GB | 2102398 | 2/1983 |
| JP | S576863 | 1/1982 |
| JP | S59133877 | 8/1984 |
| JP | S6088562 | 5/1985 |
| JP | S63255057 | 10/1988 |
| JP | H0231967 | 2/1990 |
| JP | H02102659 | 4/1990 |
| JP | H0528351 | 2/1993 |
| JP | H0645671 | 2/1994 |
| JP | H06121499 | 4/1994 |
| JP | H0938198 | 2/1997 |
| JP | H10512946 | 12/1998 |
| JP | H11500941 | 1/1999 |
| JP | H1147272 | 2/1999 |
| JP | 2000279527 | 10/2000 |
| JP | 2000514671 | 11/2000 |
| JP | 2001104486 | 4/2001 |
| JP | 2002505927 | 2/2002 |
| JP | 2002516160 | 6/2002 |
| JP | 2003047272 | 2/2003 |
| JP | 2003518984 | 6/2003 |
| JP | 2006500076 | 1/2006 |
| JP | 2007500039 | 1/2007 |
| JP | 2009539562 | 11/2009 |
| WO | 9206732 | 4/1992 |
| WO | 9516480 | 6/1995 |
| WO | 9617190 | 6/1996 |
| WO | 9623158 | 8/1996 |
| WO | 9723255 | 7/1997 |
| WO | 09726931 | 7/1997 |
| WO | 9726931 | 7/1997 |
| WO | 9822178 | 5/1998 |
| WO | 9942166 | 8/1999 |
| WO | 0006230 | 2/2000 |
| WO | 0044419 | 8/2000 |
| WO | 03084832 | 10/2003 |
| WO | 2005023355 | 3/2005 |
| WO | 2007146586 | 12/2007 |
| WO | 2008051647 | 5/2008 |
| WO | 2009112838 | 9/2009 |
| WO | 2009143116 | 11/2009 |
| WO | 2011008689 | 1/2011 |
| WO | 2011062767 | 5/2011 |
| WO | 09723255 | 12/2011 |
| WO | 2014014602 | 1/2014 |
| WO | 2014153302 A1 | 9/2014 |

OTHER PUBLICATIONS

Herts et al., "Power injection of contrast media using central venous catheters: feasibility, safety, and efficacy," AJR Am. J. Roentgenol., vol. 176, No. 2, pp. 447-453 (2001) 8 pages.

Roth et al., "Influence of radiographic contrast media viscosity to flow through coronary angiographic catheters," Cathet. Cardiovasc. Diagn., vol. 22, No. 4, pp. 290-294 (1991) 5 pages.

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of power injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahoud et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

(56) References Cited

OTHER PUBLICATIONS

Saito et al., "Diagnostic brachial coronary arteriography using a power-assisted injector and 4 French catheters with new shamps," J. Invasive Cardiol., vol. 9, No. 7pp. 461-468 (1997).
Examination Report dated Apr. 6, 2006 for European Patent Application No. 04751644.8 (5 pages).
English Translation of Office Action dated Aug. 18, 2009 for Japanese Patent Application No. 2006-517107 (3 pages).
English Translation of Office Action dated Mar. 29, 2010 for Japanese Patent Application No. 2006-517107 (2 pages).
English Translation of Office Action dated Jan. 28, 2011 for Japanese Patent Application No. 2006-517107 (3 pages).
International Search Report and Written Opinion dated Nov. 5, 2004 for International Application No. PCT/US2004/014344 (9 pages).
International Preliminary Report on Patentability dated Jan. 3, 2006 for International Application No. PCT/US2004/014344 (7 pages).
Elastomer. (2003). In The Macmillan Encyclopedia. Basingstoke, Hampshire: Macmillan Publishers Ltd. Retrieved Feb. 23, 2009 from http://www.credoreference.com/entry/3298087/.
Biffi, et al., A Randomized, Prospective Trial of Central Venous Ports Connected to Standard Open-Ended or Groshong Catheters in Adult Oncology Patients, American Cancer Society, pp. 1204-1212, May 2001.
Hoffer et al., Peripherally Inserted Central Catheters with Distal versus Proximal Valves: Prospective Randomized Trial, Society of Interventional Radiology, pp. 1173-1177, vol. 12 No. 10, Oct. 2001.
McMahon, Evaluating New Technology to Improve Patient Outcomes, pp. 250-255, vol. 25, No. 4, Jul./Aug. 2002.
Hoffer et al., Prospective Randomized Comparison of Valved Versus Nonvalved Peripherally Inserted Central Vein Catheters, pp. 1393-1398, May 1999.
Aw et al., Incidence and Predictive Factors of Symptomatic Thrombosis Related to Peripherally Inserted Central Catheters in Chemotherapy Patients, (2012), pp. 323-326.
Burns, The Vanderbilt PICC Service: Program, Procedural, and Patient Outcomes Successes, (2005), pp. 1-10, vol. 10 No. 4.
Carlo et al., A prospective Randomized Trial Demonstrating Valved Implantable Ports Have Fewer Complications and Lower Overall Cost Than Nonvalved Implantable Ports, (Aug. 7, 2004), pp. 722-727.
Corrected Notice of Allowability dated Oct. 27, 2020 for U.S. Appl. No. 16/164,229 (pp. 1-6).
Examination Report dated Aug. 12, 2010 for European Patent Application No. 05722427.1 (6 pages).
Examination Report dated Mar. 26, 2010 for European Patent Application No. 05722427.1 (5 pages).
Extended Search Report dated Sep. 21, 2011 for European Patent Application No. 11173038.8 (5 pages).
International Search Report PCT-US-05-011244—ISR dated Jun. 6, 2005.
International Preliminary Report on Patentability dated Jul. 31, 2006 for International Application No. PCT/US2005/001244 (8 pages).
International Preliminary Report on Patentability dated Nov. 232010 for International Application No. PCT/US2009/044468 (7 pages).
International Search Report 10800375_SESR dated Jul. 10, 2014.
International Search Report 10800375-7_ESC dated Jul. 17, 2017.
International Search Report 11158827-3_ESO dated May 19, 2011.
International Search Report 11158827—ESR dated May 11, 2011.
International Search Report and Written Opinion dated Dec. 23, 2009 for International Application No. PCT/US2009/044468 (10 pages).
International Search Report and Written Opinion dated Jun. 6, 2005 for International Application No. PCT/US2005/001244 (12 pages).
International Search Report and Written Opinion dated Sep. 3, 2010 for International Application No. PCT/US2010/041698 (10 pages).
International Search Report PCT-US-05-000761 IPRP dated Jul. 31, 2006.
International Search Report PCT-US-05-000761 ISR dated Dec. 4, 2005.
International Search Report PCT-US-05-000761—WOSA dated Jul. 29, 2006.
International Search Report PCT-US-05-001244 IPRP dated Jul. 31, 2006.
International Search Report PCT-US-09-044468 IPRP dated Nov. 23, 2010.
International Search Report PCT-US-09-044468 ISR dated Dec. 23, 2009.
International Search Report PCT-US-09-044468—WOSA dated Nov. 25, 2010.
International Search Report PCT-US-10-041698 ISR dated Sep. 2009.
International Search Report PCT-US-10-041698—ISR dated Dec. 2010.
International Search Report PCT-US 10-041698 IPRP dated Jan. 17, 2012.
International Search Report PCT-US 10-041698—IPRP dated Nov. 17, 2012.
Johnston et al., The Effect of Peripherally Inserted Central Catheter (PICC) Valve Technology on Catheter Occlusion Rates—The 'ELeCTRiC' Study, (2012), pp. 421-425.
Moureau, Nancy L., Glenda L. Dennis, Elizabeth Ames, and Robyn Severe. "Electrocardiogram (EKG) Guided Peripherally Inserted Central Catheter Placement and Tip Position: Results of a Trial to Replace Radiological Confirmation." Journal of the Association for Vascular Access 15.1 (2010): 8-14. Web.
Notice of Allowance dated Sep. 28, 2022 for U.S. Appl. No. 17/115,347 (pp. 1-8).
Notice of Allowance dated Nov. 30, 2022 for U.S. Appl. No. 15/240,430 (pp. 1-10).
Notice of Allowance dated Aug. 21, 2020 for U.S. Appl. No. 16/229,469 (pp. 1-5).
Notice of Allowance dated Jun. 17, 2020 for U.S. Appl. No. 16/229,469 (pp. 1-5).
Notice of Allowance dated Sep. 10, 2020 for U.S. Appl. No. 16/164,229 (pp. 1-9).
Notice of Allowance dated Feb. 14, 2011 for European Patent Application No. 05722427.1 (6 pages).
Office Action dated Nov. 16, 2021 for U.S. Appl. No. 15/240,430 (pp. 1-17).
Office Action dated Jun. 7, 2011 for Canadian Patent Application No. 2,553,335 (4 pages).
Ong et al., Prospective Randomized Comparative Evaluation of Proximal Valve Polyurethane and Distal Valve Silicone Peripherally Inserted Central Catheters, (Aug. 2010), 1191-1196.
Pittiruti et al., A Prospective, Randomized Comparison of Three Different Types of Valved and Non-Valved Peripherally Inserted Central Catheters, pp. 519-523. (1999).
Poli et al., A Comparative Study on the Mechanical Behavior of Polyurethane PICCs, pp. 175-181. (2016).
Ricchezza et al., A Strategy for Reducing Catheter Occlusions and Infections: The Experience at St. Joseph's Hospital, (2009).

\* cited by examiner

PRESSURE ACTUATED VALVE WITH IMPROVED BIASING MEMBER

BACKGROUND INFORMATION

Many medical procedures require repeated and prolonged access to a patient's vascular system. For example, during dialysis treatment blood may be removed from the body for external filtering and purification, to make up for the inability of the patient's kidneys to carry out that function. In this process, the patient's venous blood is extracted, processed in a dialysis machine and returned to the patient. The dialysis machine purifies the blood by diffusing harmful compounds through membranes, and may add to the blood therapeutic agents, nutrients etc., as required before returning it to the patient's body. Typically the blood is extracted from a source vein (e.g., the vena cava) through a catheter sutured to the skin with a distal needle of the catheter penetrating the source vein.

It is impractical and dangerous to insert and remove the catheter for each dialysis session. Thus, the needle and catheter are generally implanted semi permanently with a distal portion of the assembly remaining within the patient in contact with the vascular system while a proximal portion of the catheter remains external to the patient's body. The proximal end is sealed after each dialysis session has been completed to prevent blood loss and infections. However, even small amounts of blood oozing into the proximal end of the catheter may be dangerous as thrombi can form therein due to coagulation which thrombi may then be introduced into the patient's vascular system when blood flows from the dialysis machine through the catheter in a later session.

A common method of sealing the catheter after a dialysis session is to shut the catheter with a simple clamp. This method is often unsatisfactory because the repeated application of the clamp may weaken the walls of the catheter due to the stress placed on the walls at a single point. In addition, the pinched area of the catheter may not be completely sealed allowing air to enter the catheter which may coagulate any blood present within the catheter. Alternatively, valves have been used at the opening of the catheter in an attempt to prevent leaking through the catheter when the dialysis machine is disconnected. However, the unreliability of conventional valves has rendered them unsatisfactory for extended use.

SUMMARY OF THE INVENTION

The present invention is directed to a valve for controlling material flow through a catheter, comprising a first flexible member including a first moveable element, wherein, when the first moveable element is in the open position, material may flow past the first flexible member through a first lumen of the catheter and, when the first moveable element is in the closed position, flow through the first lumen is prevented and a first biasing member coupled to the first flexible member for biasing the first moveable member toward the closed position.

DETAILED DESCRIPTION

Semi-permanently placed catheters may be useful for a variety of medical procedures which require repeated access to a patient's vascular system in addition to the dialysis treatments mentioned above. For example, chemotherapy infusions may be repeated several times a week for extended periods of time. For safety reasons, as well as to improve the comfort of the patient, injections of these therapeutic agents may be better carried out with an implantable, semi-permanent vascular access catheter. Many other conditions that require chronic venous supply of therapeutic agents, nutrients, blood products or other fluids to the patient may also benefit from implantable access catheters, to avoid repeated insertion of a needle into the patient's blood vessels. Thus, although the following description focuses on dialysis, those skilled in the art will understand that the invention may be used in conjunction with any of a wide variety of procedures which require long term implantation of catheters within the body.

Examples of such implantable catheters include those manufactured by Vaxcel™, such as the Chronic Dialysis Catheter and the Implantable Vascular Access System. These devices typically are inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations.

Figure 1:
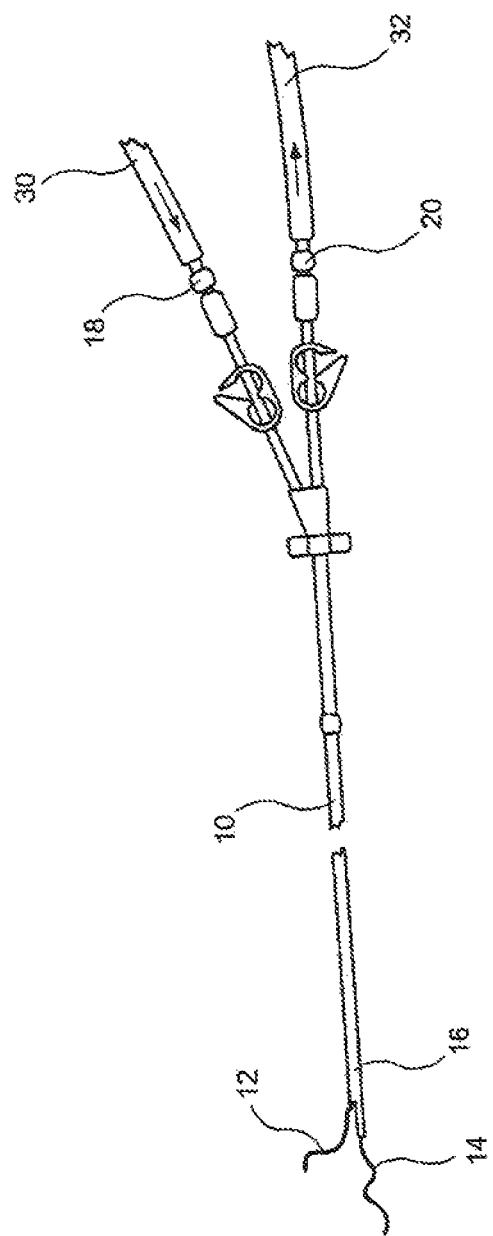
FIG. 1 is a schematic diagram of a vascular access catheter.
Figure 2:
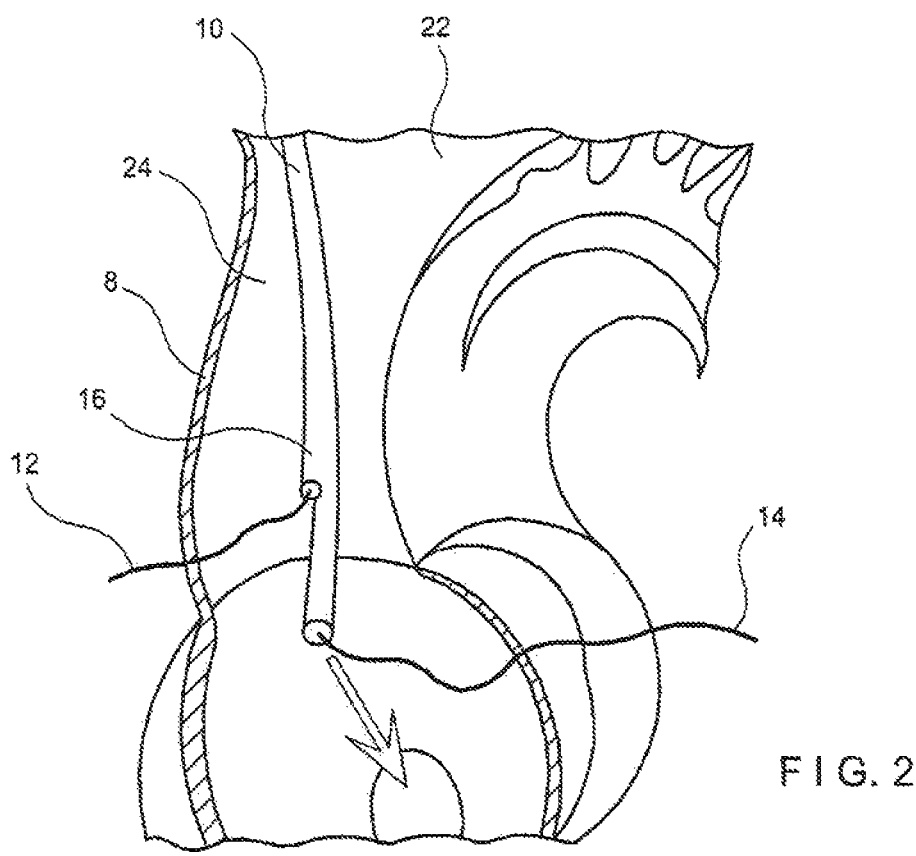
FIG. 2 is a schematic drawing of a vascular access catheter inserted in a patient's vein.

FIGS. 1 and 2 show an exemplary implantable catheter for kidney dialysis. Catheter 10 has a distal end 12 that is insertable under the skin and into the patient's vein, and which remains within the patient's body for the life of the catheter 10. For example, catheter 10 may remain implanted in the patient for two years. As shown more clearly in FIG. 2, distal end 12 fits within a vein 8 (e.g., the vena cava). During dialysis, blood from the patient is removed through a patient line such as catheter 10, and is purified by a dialysis machine (not shown) which is connected to hubs 18 and 20 of catheter 10 by a dialysis line. Catheter 10 in this example includes two lumens 22 and 24 which are used respectively to remove blood from and reintroduce blood to the vessel 8. Lumen 22 terminates at an inflow tip 14 formed at the distal end 12 of the catheter 10 while lumen 24 terminates at an outflow tip 16 formed at the distal end 12. Inflow tip 14 and outflow tip 16 are connected to corresponding inflow and outflow hubs 18, 20, which are accessible outside the body and which may be connected to external lines leading to and from the dialysis machine.

After the dialysis or other procedure has been completed, the catheter 10 is disconnected from the dialysis machine, and is left within the patient fluidly coupled to the patient's vascular system. When not connected to a dialysis machine, the catheter 10 is securely sealed to prevent fluids and gases from crossing into the proximal end of catheter 10 by preventing flow in and out of catheter 10 through hubs 18, 20. As would be understood by those skilled in the art, this sealing prevents the risks associated with infections and thrombi which might be experienced if air or other gas or liquid and/or pathogens were to pass into the catheter 10.

As indicated above, although conventional clamps or clips may be used to seal the catheter 10 between medical sessions, over time the wall of the catheter 10 may be damaged in the area to which the clamp or clip is applied. Sealing clamps or clips may also become dislodged during patient activities, increasing the risk of leaks, infections, etc. Placing a clamp on the catheter 10 also increases the bulk of the distal end of the catheter which is exposed outside the patient's body, and may adversely affect patient comfort.

Therefore, the catheter 10 includes one or more self sealing valves along each of the lumens 22, 24 to seal them when not being used during dialysis and other transfusion or infusion sessions. For example, hubs 18, 20 may be used to house one or more valves each of which is designed to seal the corresponding lumen 22, 24 under certain conditions, and to allow passage of fluids under other conditions. For example, in the case of dialysis treatment, the system of valves may seal the catheter 10 when it is not connected to an operating dialysis machine, and may allow both an outflow of non-purified blood and an inflow of purified blood to the patient when an operating dialysis machine is connected thereto.

Preferably, a valve system for use in such semi-permanent catheters should, when in the open position, allow a flow rate therethrough which is sufficient to allow the procedure to be completed in an acceptably short time. When in the closed position, the valve should completely seal the catheter. That is, if the valve requires excessive force to be opened, the flow rate through the catheter may be reduced to the point where the time required for the procedure is unacceptably extended. In addition, a valve system having moving parts of too great a bulk may also result in larger blockages within the catheter or the hub housing the valve thereby reducing the flow rate through the catheter. The mechanism that moves the valve into the open and closed positions may block the flow through the valve if it protrudes into the flow passage, and thus the size and bulk of the mechanism should preferably be minimized to avoid impeding flow through the open valve.

The portion of the valve that moves to the open position must also completely return to the closed position when the session is completed. For example, a pressure sensitive valve may be used, which opens in response to a pressure driving the flow through the catheter. In the case of a dialysis catheter, the valve or valves may open when a pressure generated by the dialysis machine exceeds a predetermined threshold to allow circulation and purification of the patient's blood. When the dialysis machine is turned off and the pressure in the dialysis line is reduced below the threshold, the valve is completely sealed to prevent further flow from and to the patient. Some pressure is also present in the patient line connecting the valve to the patient's vein as a result of the circulation in the patient's vascular system. Each of the valves must therefore be designed so that it will not respond to such pressure variations introduced by the vascular system and will not open unless a pressure above the threshold is generated externally, for example, by a dialysis machine.

The exemplary embodiments according to the present invention described herein obtain both a secure closure of a semi-permanent catheter implanted in a patient when the catheter is not in use and permit a flow passage that is easily opened to allow a sufficient flow rate when access to the vascular system is necessary.

In many applications, the pressure actuated valve system remains open for the entire length of a therapeutic session, which may last a significant amount of time. For example, in the case of a dialysis session, the valve system may remain open for up to four hours at a time, during sessions carried out up to three times a week. The exemplary embodiments of valves according to the present invention provide a seal to the catheter even after being maintained in the open position for prolonged periods of time.

Figure 3:
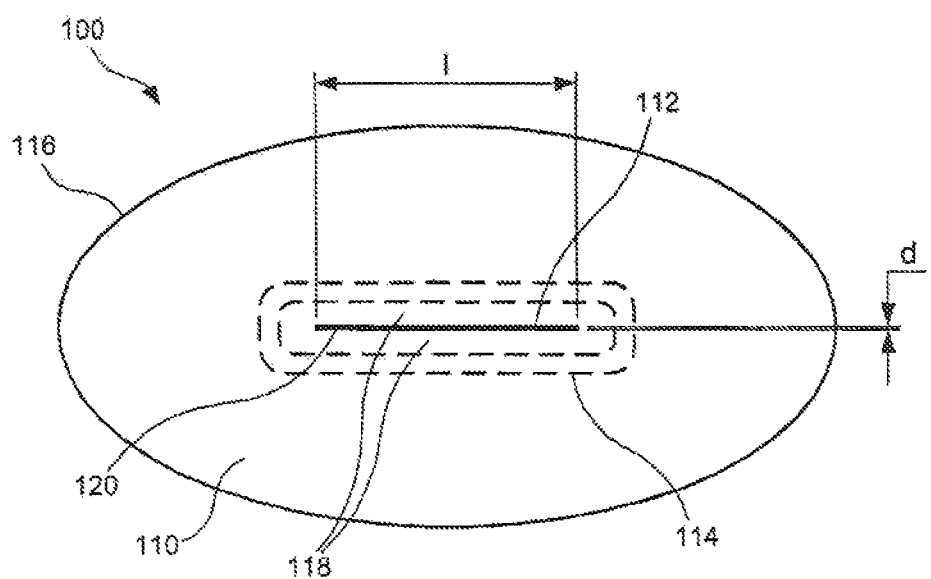
FIG. 3 is a top elevation view of a valve device according to an exemplary embodiment of the present invention.

Specific embodiments of the present invention will be described below with reference to the drawings. FIG. 3 shows a top plan view of an exemplary embodiment of a valve element 100 used to control the flow through a medical tube such as the catheter 10 of FIG. 1. For example, valve element 100 may be located in a flow passage within a valve housing formed in either or both of the hubs 18, 20, through which fluids flow to and from the distal end 12. As will be apparent to those skilled in the art, the valve housing may be placed at any other location along the length of catheter 10 and may be unitary with the catheter 10, or may be formed as a separate component. In addition, it will be apparent that a single valve housing with dual flow passages and one valve 100 within each of the flow passages may be provided instead of two separate valve housings for the hubs 18, 20, respectively, to independently control fluid flow in each direction. Inflow to the patient may take place via one of the dual flow passages of the single hub, and outflow from the patient via the other flow passage.

In the exemplary embodiment shown in FIG. 3, the valve element 100 is formed as a flexible disk 110 having dimensions appropriate to the size of the flow passage within the one of the hubs 18, 20 into which it is to be mounted. The flexible disk 110 may be formed of any sufficiently flexible material, such as a polymeric material. More specifically, the flexible disk 110 may be formed of silicone. The flexible disk 110 may also include a peripheral portion 116 adapted to be connected to an inner surface of the flow passage to seal perimeter of the flow passage around flexible disk 110. The valve element 100 includes a slit 112 which is extends through the entire thickness of the flexible disk 110. The slit 112 separates two movable elements 118 from one another to form an openable portion of the disk 110 which creates a flow passage therethrough when the movable elements 118 are placed in an open position separated from one another. For example, when the edges 120 of the movable elements 118 are moved out of the plane of the flexible disk 110, an opening through the flexible disk 110 is formed along the slit 112. In this exemplary embodiment, the movable elements 118 are formed as resilient flaps substantially constrained in all directions except along the slit 112. Accordingly, the elements 118 are substantially constricted and may only move along the edges 120 to form a relatively small opening.

In one exemplary embodiment the valve element 100 is used in conjunction with dialysis equipment, and movement of movable elements 118 to the open position is prompted by an actuating pressure of a fluid within dialysis lines 30, 32 which may be connected to the hubs 18, 20, respectively, to connect the catheter 10 to a dialysis machine. In particular, an actuating pressure is generated by pumps in the dialysis machine to move the patient's blood between the patient and the filtration equipment. Although the movable elements 118 are formed as flexible flaps, they are formed with a predetermined amount of resilience to allow them to remain in the closed position when not acted upon by the pressure in dialysis lines 30, 32. Specifically, the elements 118 are biased to remain in the closed position abutting one another along edges 120 at all times when they are not acted on by a pressure outside a range of approximately 22 to 44 mmHg. Specifically, as mentioned above, the elements 118 are formed so that the amount of resilience is sufficient to maintain them in the closed position without being forced open by fluid forces generated by natural circulation of the patient's blood. As would be understood by those skilled in the art, the amount of pressure required to open the movable elements 118 is a function of the resilience of the material forming those elements, the size and shape of the slit 112, and the size of the flow passage containing the valve element 100. The details of the geometry of the slit 112 and the movable elements 118 may be selected to obtain the desired characteristics of maximum flow in the open position, and to ensure that valve element 100 seals the flow passage when the pressure is removed.

A stiffening element 114 may be included in valve element 100, to better control the amount of force biasing the movable elements 118 to the closed position. In particular, coupling a stiffening element to an otherwise flexible disk 110 (or forming a stiffening element integrally therewith) provides a valve element 100 including movable elements 118 more resistant to plastic deformation during sessions lasting multiple hours in which the valve element 100 is kept open. An example of a suitable stiffening member is the addition of stiffening ring 114 to the flexible disk 110. The stiffening element 114 may, for example, be formed of a wire embedded within the valve element 100. Of course, those skilled in the art will understand that the stiffening element 114 may be formed of metal, plastic or any substantially rigid material.

In one exemplary embodiment, the stiffening ring 114 may be embedded within the material of the disk 110, to minimize the bulk of the combination. In different embodiments, stiffening elements may be bonded to one or both sides of the valve element 100, depending on the requirements of the use of the valve element 100. The shape of the stiffening elements used in the valve element 100 may also be modified, depending on the desired characteristics of the force urging the movable elements 118 to the closed position. Alternatively, the stiffening elements may be integrally formed with the disk 110.

As indicated above, the maximum flow that can pass through valve element 100 and the ability to close fully when the actuating pressure is removed are important design parameters for the pressure actuated valves described herein. According to embodiments of the invention, these design parameters may be controlled by properly shaping and sizing the slit or slits 112. Selection of the dimensions of the slit 112 results in movable elements 118 having a desired shape and being constrained along selected edges. In the exemplary embodiment shown in FIG. 3, a linear slit having a width d of approximately 0.002 inches and a length of approximately 0.150 to 0.280 inches is provided in the center of an oval flexible disk 110 extending along a major axis of the disk. The flexible disk 110 could have a thickness of approximately 0.015 to 0.030 inches and could be manufactured from silicone, as a result its surface resistivity rating would be approximately 35 to 70 A. The movable elements 118 used in this configuration are flaps that form an opening by deflecting away from the plane of the disk 110 due to their flexibility, since they are constrained along all sides except along the slit 112. This configuration provides satisfactory performance in a dialysis catheter application, with the catheter having conventional dimensions and providing conventional flow rates. For example, the pressure to which the valve may be subjected during dialysis may be in the range of 200 to 285 mmHg while the pressures applied to the valve by the patient's vascular system are expected to remain below 22 mmHg. Thus, the valve system will preferably be designed to remain sealed when not subjected to a pressure of at least 44 mmHg and, when subjected to the a pressure above that threshold should preferably allow a flow rate of at least 300 ml/min and more preferably at least 350 ml/min without substantially failing to meet these criteria during a life span of one or more years while being subjected to 3 or more uses of up to 4 hours each per week.

The performance characteristics of the valve element 100 can be further tuned by selecting an appropriate length l of the slit 112. By altering this length l, both the maximum flow rate and the opening/closing performance of the valve element 100 will be changed. For example, increasing the length of the slit 112, other parameters being the same, increases a maximum size of the opening through the flexible disk 110, and makes it easier to displace the movable elements 118 to the open position as they are unconstrained along longer edges 120. For the same reason, the movable elements 118 are subjected to a reduced force biasing them toward the closed position when the actuating pressure is removed. Both the width d and the length l of the silt 112 are selected as a tradeoff between ease/size of the opening and the biasing force closing the valve element 100 after use.

Figure 4:
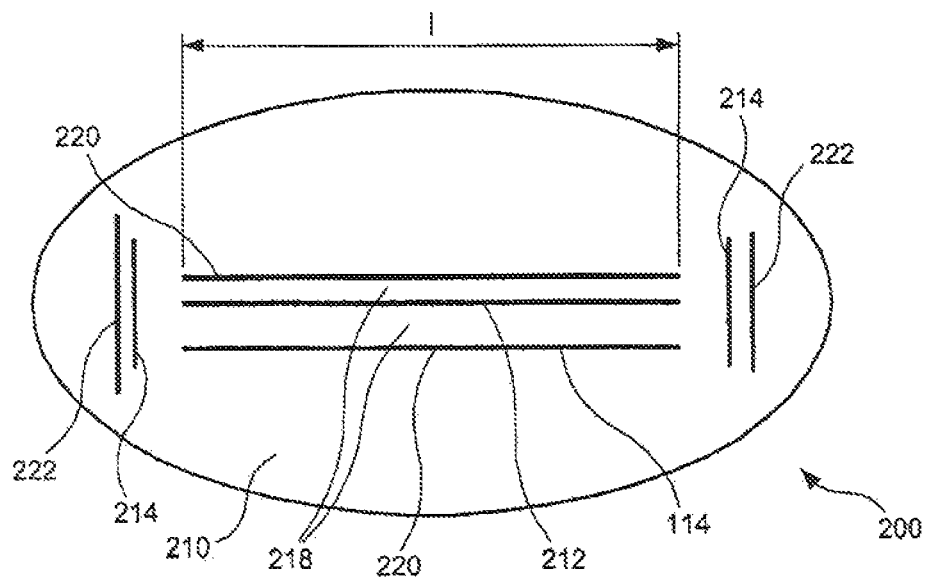
FIG. 4 is a top elevation view of a valve device according to another embodiment of the present invention.

A different exemplary configuration of slits to define the movable elements is shown in FIG. 4. In this embodiment, a flexible disk 210 is provided with slits 212, 214 in a substantially H-shaped configuration that define movable elements 218. The slit 212 is a substantially linear slit aligned with a major dimension of the disk 210, and the slits 214 extend substantially perpendicular to slit 212, disposed near terminating points thereof. This configuration of slits permits the movable elements 218 to more easily move to the open configuration, since each movable element 218 is unconstrained along both the slit 212 and the slits 214. The pressure generated by an external pump, such as a dialysis pump, thus can more easily force the movable elements 218 to the open position. The two additional unconstrained sides of the movable elements 218 also form a larger open area of flexible disk 210, so that a greater flow rate can pass through the valve element 200.

Additional resilient elements may also be used in the exemplary embodiment shown in FIG. 4 to achieve desired closing characteristics of the valve element 200. For example, a pair of resilient elements 220 may be disposed substantially parallel to the slit 212 on either side thereof. The resilient elements 220 control the deflection and provide a force biasing the movable elements 218 toward the closed position along the axis of the slit 212. Those skilled in the art will understand that additional resilient elements 222 may be used to increase the biasing force and/or to control the deflection of the movable elements 218 along an axis parallel to the slits 214. This exemplary combination of H-configured slits and corresponding H-configured resilient elements results in a high flow, easily opened pressure actuated valve element 200, which is able to completely return to the closed position once the actuating pressure is removed. This configuration also resists plastic deformation that may occur when valve elements are kept in the open position for extended periods of time, and which may prevent the valve from fully closing due to retaining a "memory" of the open position.

Figure 5:
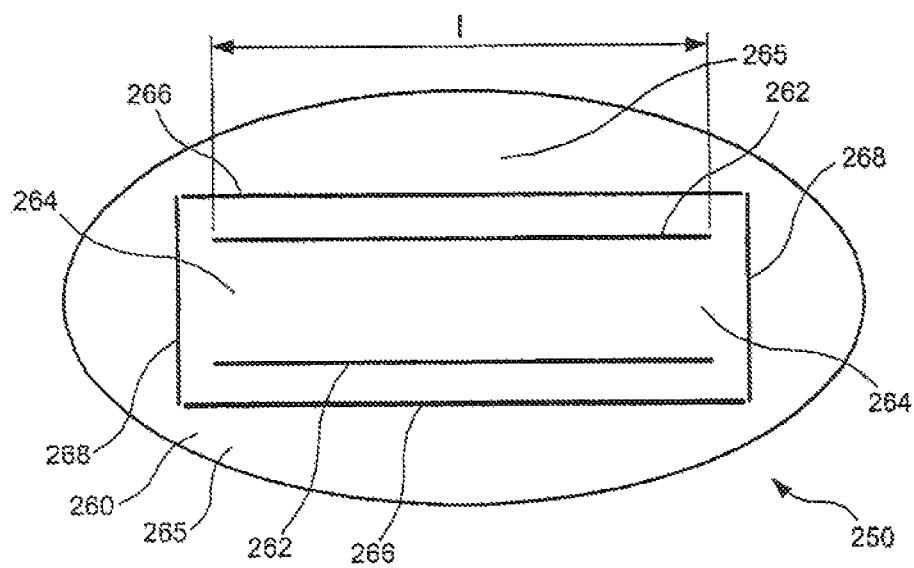
FIG. 5 is a top elevation view of a valve device with double horizontal slits according to an embodiment of the present invention.

Another exemplary embodiment according to the present invention is depicted in FIG. 5. In this embodiment, a double horizontal slit is used to define the movable elements of a valve element 250. More specifically, a pair of substantially parallel slits 262 extend through the flexible disk 260, substantially along a major dimension thereof. In the case of a substantially elliptical flexible disk 260, as shown, the slits 262 are substantially parallel to a major axis of the ellipse. A movable element 264 is thus defined substantially at the center of the flexible disk 260, and is constrained only at ends 265 thereof near termination points of the slits 262.

The greater unconstrained length of the sides of the movable element 264 along the slits 262, enables a large flow area to open as a result of an actuating pressure. For the same reason, a relatively low actuating pressure is needed to open the movable element 264. To ensure a complete closing of the valve element 250 when the actuating pressure is removed, for example, resilient elements may be added around the slits 262 to further bias the movable element 264 to the closed position. In the exemplary embodiment shown in FIG. 5, resilient elements 266, 268, which may comprise, for example, wires embedded within the valve element 250, are disposed in a substantially rectangular configuration surrounding the slits 262. In this configuration the resilient elements 266, 268 control the deflection of the movable element 264 in directions substantially parallel and perpendicular to the slit orientation and provide a biasing force that closes the movable element 264 when the actuating pressure is removed. The resilient elements 266, 268 may form a complete rectangle, or may be separated at the vertices.

Figure 6:
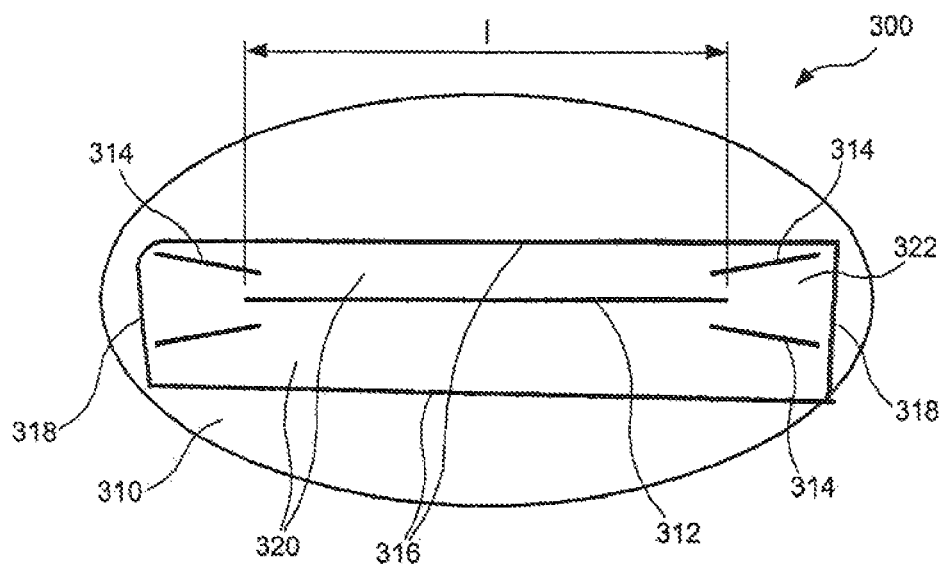
FIG. 6 is a top elevation view of a valve device with Y-configured slits according to an embodiment of the present invention.

FIG. 6 shows yet another embodiment of the pressure actuated valve according to the present invention. In this exemplary embodiment, a linear slit is combined with a pair of Y-configured slits to provide a larger flow area when a valve element 300 is placed in the open position by an actuating pressure thereagainst. As shown in the drawing, the valve element 300 is formed as a flexible disk 310 which, in this example, has a substantially elliptical shape. It will be apparent to those skilled in the art that different shapes of the flexible disk 310 may be used, depending on the shape and dimensions of the housing within which the valve element 300 is to be placed. A substantially linear slit 312 is formed in the flexible disk 310, for example along a major dimension thereof, and is complemented by two pairs of slits 314. A first pair of the slits 314 is disposed at a first end of the slit 312 with a second pair of slits 314 being formed at the second end of the slit 312. The slits 314 are formed at an angle with the slit 312, so that, at each end of the slit 312, a substantially Y-shaped configuration of slits is formed.

In the exemplary embodiment shown, the slits 312 and 314 do not touch one another so that the movable elements 320 are continuous with portions 322 of the flexible disk 320. In different embodiments, the slits 312 and 314 may intersect with one another, breaking the flexible disk 320 into additional distinct moving elements. In the exemplary embodiment shown, the movable elements 320 are unconstrained along the slits 312, 314, but are constrained in the region between the slits by being continuous with the portions 322 of the flexible disk 320. The addition of the Y-configured slits permits the movable elements 320 to open to a greater extent under an equivalent actuating pressure, while retaining a biasing force sufficient to completely close the opening when the actuating pressure is removed. To further bias the movable elements 320 toward the closed position, resilient elements 316, 318 may be added. As discussed in the context of previous embodiments, the resilient elements 316, 318 may be disposed in a substantially rectangular pattern around the slits 312, 314 to control the deflection and closure of the movable elements 320 in two directions substantially perpendicular to one another. The resilient elements 316, 318 may form a completely rectangular enclosure as shown in FIG. 6, or may have open vertices, as shown in previous embodiments. As would be understood by those skilled in the art, the relative size and orientation of the slits 312, 314 may be selected to give desired flow and closing properties, for a given flexible disk 320.

Figure 7:
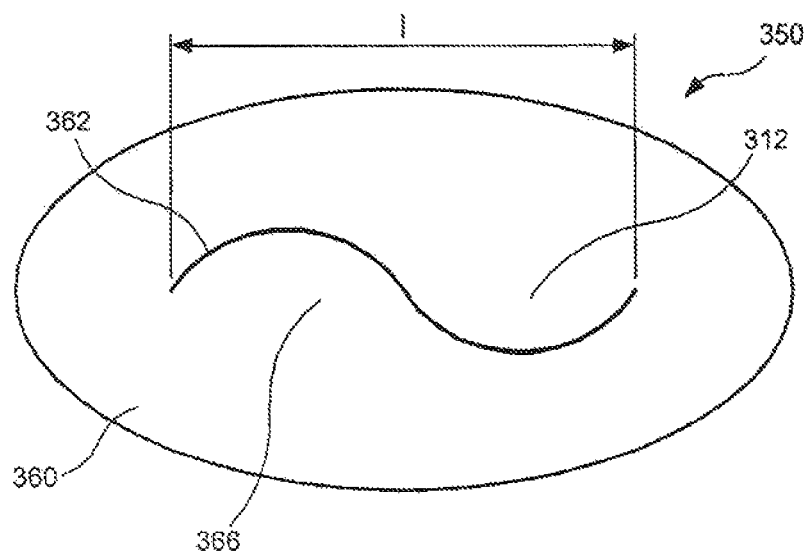
FIG. 7 is a top elevation view of a valve device with a curved slit according to an embodiment of the present invention.

A different exemplary embodiment according to the present invention is depicted in FIG. 7. In this example, a valve device 350 comprises a flexible disk 360 having a slit 362 formed therein. The slit 362 is not formed as a linear slit, but instead is curved about a principal axis of the flexible disk 360. In the example shown in FIG. 7, the slit 362 follows a substantially sinusoidal path. However other curved paths may be used with similar effect. The sift 362 defines two movable elements 364, 366 which are complementary to each other along the slit 362. A benefit of this configuration is that for a given length l of the slit 362, a larger opening area of the valve device 350 is obtained as compared to linear slit designs. Since the unconstrained edges of the movable elements 364, 368 are longer due to their curved shape of the slit 362, a given actuating pressure displaces a larger portion of the movable elements 364, 366 to the open position. Thus, this design allows a larger flow area through the valve device 350.

As was the case in other the exemplary embodiments of the invention, the resilience of the movable elements 364, 366 is controlled to ensure that the valve element 350 fully closes once the actuating pressure is removed—even after remaining open for extended periods of time (i.e., to ensure that the valve is not subject to "memory" effects). Accordingly, the resilience of the material forming the movable elements 364, 366 is preferably selected and additional resilient elements are incorporated into the flexible disk 360, as described above with respect to other embodiments, based on the conditions to which the valve element 350 is to be subjected to ensure that such plastic deformation does not result in degraded performance over time.

The present invention has been described with reference to specific exemplary embodiments. Those skilled in the art will understand that changes may be made in details, particularly in matters of shape, size, material and arrangement of parts. For example, different flexible disks may be used to form the pressure sensitive valve, and may have different dimensions than those shown. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed:

1. A valve comprising:
   a flexible member comprising a first moveable element, a second movable element, and at least one biasing member;
   wherein the first moveable element and the second moveable element are configured to remain in a closed position when acted upon by a predetermined fluid pressure; and
   wherein the at least one biasing member is configured to bias the first moveable element and the second moveable element towards the closed position.

2. The valve of claim 1, wherein the predetermined threshold level of fluid pressure is below 44 mmHG.

3. The valve of claim 1, wherein the first moveable element and the second moveable element are configured to move to an open position when acted upon by a flow of fluid above the predetermined fluid pressure.

4. The valve of claim 1, wherein the valve is sized to fit within a flow passage of a catheter hub.

5. The valve of claim 4, wherein the flexible member is substantially an elliptical shape.

6. The valve of claim 1, wherein the valve is configured to allow a flow rate of up to 350 ml/min.

7. The valve of claim 1, wherein the at least one biasing member is integrally formed within the flexible member.

8. The valve of claim 7, wherein the at least one biasing member comprises two biasing members both comprised of a plastic material.

9. The valve of claim 7, wherein the at least one biasing member comprises two biasing members both comprised of a metal material.

10. The valve of claim 7, wherein the at least one biasing member is configured to control the amount of force biasing the first moveable element and the second moveable element towards the closed position.

11. The valve of claim 1, wherein the flexible member comprises a major axis.

12. The valve of claim 11, wherein the first movable element and the second movable element are configured to be substantially parallel to the major axis.

13. A valve comprising:
a flexible member comprising a first moveable element, a second movable element, and two biasing members;
wherein the first moveable element and the second moveable element are configured to remain in a closed position when acted upon by a predetermined fluid pressure; and
wherein the two biasing members are configured to bias the first moveable element and the second moveable element towards the closed position; and wherein the two biasing members are integrally formed within the flexible member.

14. The valve of claim 13, wherein the predetermined threshold level of fluid pressure is below 44 mmHG.

15. The valve of claim 13, wherein the flexible member is substantially an elliptical shape.

16. The valve of claim 13, wherein the flexible member comprises a major axis.

17. The valve of claim 16, wherein the first movable element, the second movable element, and the biasing member are configured to be substantially parallel to the major axis.

18. A valve comprising:
a flexible member comprising a first moveable element, a second movable element, and a biasing member;
wherein the first moveable element and the second moveable element are configured to remain in a closed position when acted upon by a fluid flow below a predetermined fluid pressure; and
wherein the biasing member is configured to bias the first moveable element and the second moveable element towards the closed position;
wherein the biasing member is integrally formed within the flexible member; and
wherein the flexible member is substantially elliptically shaped comprising a major axis.

19. The valve of claim 18, wherein the first movable element, the second movable element, and the biasing member are configured to be substantially parallel to the major axis.

20. The valve of claim 18, wherein the flexible member further comprises a slit.

* * * * *